United States Patent [19]

Igarashi

[11] Patent Number: 5,395,756
[45] Date of Patent: Mar. 7, 1995

[54] PRODUCTION OF ACIDIC FGF PROTEIN

[75] Inventor: Koichi Igarashi, Kyoto, Japan

[73] Assignee: Takeda Chemical Industries, Ltd., Osaka, Japan

[21] Appl. No.: 222,187

[22] Filed: Apr. 4, 1994

Related U.S. Application Data

[63] Continuation of Ser. No. 14,003, Feb. 5, 1993, abandoned, which is a continuation of Ser. No. 547,818, Jul. 2, 1990, abandoned.

[30] Foreign Application Priority Data

Jul. 3, 1989 [JP] Japan .................. 1-172542
Sep. 29, 1989 [JP] Japan .................. 1-256193

[51] Int. Cl.⁶ .................. C12N 15/00; C12N 5/00
[52] U.S. Cl. .................. 435/69.4; 435/172.3; 435/240.2; 435/69.1; 435/320.1; 435/252.33
[58] Field of Search .................. 435/69.1, 69.4, 172.3, 435/240.2, 252.3, 252.33, 320.1

[56] References Cited

U.S. PATENT DOCUMENTS

| | | | |
|---|---|---|---|
| 4,952,496 | 8/1990 | Studier et al. | 435/91 |
| 5,175,147 | 12/1992 | Folkman et al. | 514/12 |

FOREIGN PATENT DOCUMENTS

| | | | |
|---|---|---|---|
| 0178863 | 10/1985 | European Pat. Off. | C12N 15/00 |
| 0259953 | 7/1987 | European Pat. Off. | C12N 15/00 |
| 0298723 | 7/1988 | European Pat. Off. | C12N 15/00 |
| 0360006 | 8/1989 | European Pat. Off. | A61K 37/36 |
| 2642086 | 1/1989 | France | C12N 15/12 |

OTHER PUBLICATIONS

Squires, C. et al., *J. Biol. Chem.*, 263 (31): 16297–16302, 1988.
Rosenberg, et al., "Vectors for selecive expression of cloned DNAs" by T7 RNA polymerase, Gene 56, 15–135 (1987).
Gimenez–Gallego, G. et al. Biochem. Biophys. Res. Commun. vol. 138, 611 (1986).
Brew, K. et al. (Eds.) ICSU Short Report 8, Advances in Gene Technology: Protein Engineering and Production; IRL Press; Washington, DC, p. 110, 1988.
Barr, P. et al., J. Biological Chemistry, 263, 16471 (1988).
Davanloo, P. et al. Proc. Natl. Acad. Sci, 81, 2035 (1984).
Studier, F. W. et al. J. Mol. Biol. 189, 113 (1986).
Watanabe, T. et al., Folia Endocrinologica Japonica vol. 66, No. 4, p. 359, Title 276.
Watanabe, T. et al., Molecular Endocrinology vol. 4, No. 6, pp. 869–879 (1990).

*Primary Examiner*—Garnette D. Draper
*Assistant Examiner*—Marianne Porta Allen
*Attorney, Agent, or Firm*—David G. Conlin; David S. Resnick

[57] ABSTRACT

An expression vector comprises a cDNA sequence encoding an aFGF protein and a T7 promoter upstream therefrom. The vector is useful for transforming host cells and expressing the aFGF gene.

6 Claims, 11 Drawing Sheets

```
Hind III          BspMI
  ↓         10    ↓  20         30         40         50         60
AAGCTTACCT GCCATGTTTA ATCTGCCTCC CGGGAATTAC AAGAAGCCCA AACTCCTCTA
           70         80         90        100        110        120
CTGCAGCAAC GGGGGCCACT TCCTGAGGAT TCTTCCGGAT GGCACAGTGG ATGGGACAAG
          130        140        150        160        170        180
GGACAGGAGC GACCAGCACA TTCAGCTGCA ACTCAGTGCG GAAAGCGTGG GGGAGGTGTA
          190        200        210        220        230        240
TATAAAGAGT ACCGAGACTG GCCAGTACTT GGCAATGGAC ACCGACGGGC TTTTATACGG
          250        260        270        280        290        300
CTCACAGACA CCAAATGAGG AATGTTTGTT CCTGGAAAGG CTGGAGGAGA ACCATTACAA
          310        320        330        340        350        360
CACCTATATA TCCAAGAAGC ATGCAGAGAA GAATTGGTTT GTTGGCCTCA AGAAGAATGG
          370        380        390        400        410        420
GAGCTGCAAA CGCGGTCCTC GGACTCACTA TGGCCAGAAA GCAATCTTGT TTCTCCCCT
          430        440        450        460        470        480
GCCAGTCTCT TCTGATTAAT AAGGATCCGA ATTC
                         ↑      ↑
                       BamHI  EcoRI
```

PRODUCTION OF ACIDIC FGF PROTEIN

This is a continuation of application Ser. No. 08/014,003, filed on 5 Feb. 1993, now abandoned, which is a continuation of application Ser. No. 07/547,818, filed on 2 Jul. 1990, now abandoned.

FIELD OF THE INVENTION

The present invention relates to a process for producing an acidic fibroblast growth factor protein. More specifically, the present invention relates to a method for the preparation of an acidic fibroblast growth factor (also, hereinafter briefly referred to as aFGF) protein which may be employed as wound healing promoting agents, which comprises
constructing a vector comprising a base sequence encoding the aFGF protein:and a T7 promoter upstream therefrom,
transforming a host with the vector, and culturing the resulting transformant in a medium.

Further, the present invention relates to a vector comprising a base sequence encoding the aFGF protein and a T7 promoter upstream therefrom.

Another aspect of the present invention relates to a transformant containing the vector.

BACKGROUND OF THE INVENTION

Acidic FGFs are a group of endothelial cell growth factors that have been observed in hypothalamus, brain, retina, etc. and that have a molecular weight of about 16000 and an isoelectric point of 5 to 7. They are characterized by the ability to bind strongly for heparin, and in general well known as a neovascularizing factor.

Methods for the preparation of aFGF by use of genetic engineering techniques have been reported in Biotechnology 5, 960 (1987); Journal of Biological Chemistry, 263, 16471 (1988); ICSU Short Reports Volume 8, Advances in Gene Technology; Protein Engineering and Production, Proceedings of the 1988 Miami Bio/Technology Winter Symposium, IRL Press, page 110; and EP No. 0319052.

It is still desirable, however, to produce aFGF by recombinant DNA techniques in higher efficiency.

SUMMARY OF THE INVENTION

In general, in order to increase the productivity of gene products by the application of genetic engineering techniques, it is necessary to select the most optimal combination of promoter, host and vector for each gene encoding the desired gene product.

In accordance with the present invention, we have synthesized chemically cDNA for human aFGF by utilizing the information with regard to the amino acid sequences of human aFGF which has been reported in the literature [F. Esch et al., Biochem. Biophys, Res, Commun. 133, 554–562, 1985], performed the expression of the cDNA in combination with various promoters, hosts and vectors, and thereby evaluated expression levels (productivities of gene products).

As a result, it has been now found that the expression system of cloned genes in *Escherichia coli* wherein a T7 promoter [F. W. Studier et al. J. Mol. Biol. 189, 113–130, 1986] is used for the expression of aFGF cDNA is most advantageous.

According to the invention, there is provided a method for the preparation of an aFGF protein which comprises, (1) constructing a vector comprising a base sequence encoding the aFGF protein and a T7 promoter upstream therefrom,
(2) transforming a host with the vector, and
(3) culturing the resulting transformant in a medium.

According to the invention, there is also provided a vector comprising a base sequence encoding an aFGF protein and a T7 promoter upstream therefrom.

Further according to the invention, there is provided a transformant having a vector comprising a base sequence encoding an aFGF protein and a T7 promoter upstream therefrom.

Also according to the invention, there is provided a method for preparing an aFGF protein which comprises culturing the transformant in a medium.

According to the present invention, aFGF proteins can be prepared efficiently by use of the vector comprising the T7 promoter and therefore the method according to the present invention is industrially useful in producing the aFGF protein.

DETAILED DESCRIPTION OF THE INVENTION

The aFGF protein which can be produced in the present invention includes a bovine aFGF, a human aFGF and the like. The amino acid sequences of bovine and human aFGFs are disclosed in Biochemical and Biophysical Research Communicaitons, Vol. 138, No. 2, pp. 611–617 (1986). The aFGF proteins which can be produced also include muteins in which a part of amino acid sequence is changed, deleted, and/or added.

The aFGF muteins in the present invention maintain, however, essentially the amino acid sequence of the orginal peptide and protein.

Such mutation may include amino acid additions of amino acid(s), deletions of constituent amino acid(s) or substitutions of constituent amino acid(s) by other amino acid(s).

Amino acid addition means adding at least one amino acid thereto.

Amino acid deletion means deleting at least one constituent amino acid therefrom.

The deleted-type muteins are preferably those comprising continuous polypeptides consisting of from 90 to 133 amino acids of aFGF, more preferably those comprising continuous polypeptides consisting of from 120 to 131 amino acids of aFGF, still more preferably those comprising continuous polypeptides consisting of from 125 to 131 amino acids of aFGF.

Such deleted-type muteins can lack up to 3 amino acids from the C-terminus of mature aFGF. Examples of said deleted-type muteins may include, for example, those lacking any of 8 amino acids, 9 amino acids, 11 amino acids, 12 amino acids, 20 amino acids and 43 amino acids from the N-terminus of human aFGF, Furthermore, the deleted-type muteins may include those which lack 5 amino acids or 1 amino acid from the N-terminus of human aFGF, those which lack 6 amino acids from the N-terminus of bovine aFGF, muteins which comprise an amino acid sequence residing either between positions 1 and 15, between 114 and 140, between 1 and 41, or between 7 and 41 of bovine aFGF (numbered from the N-terminus), those which comprise an amino acid sequence residing either between positions 1 and 41, or between 7 and 41 of human aFGF (numbered from the N-terminus), and the like.

Such substitution means substituting another amino acid for at least one of aFGF-constituent amino acids therein.

Where the mutein in the present invention has at least one amino acid added to aFGF, the at least one amino acid therein excludes methionine derived from initiator codons used for expression of peptides and signal peptides. The number of added amino acids is at least one and it may be any one as long as the mutein keeps the characteristics of aFGF. Preferably, the added amino acids may include some or all of the amino acid sequences in proteins which are accepted to be homologous with aFGF and exhibit activities similar to those of aFGF.

In a mutein which lacks at least one aFGF-constituent amino acid, the number of deleted amino acids may be any one, as long as the mutein keeps the characteristics of aFGF.

In a mutein where aFGF-constituent amino acid is substituted by other amino acid, the number of the aFGF constituent amino acids before substitution therein replaced is not limited, as long as the mutein keeps the characteristics of aFGF. Examples of the constituent amino acids before substitution may include cysteine and other amino acids, and particularly preferably, cysteine. Examples of the constituent amino acid which is other than cysteine includes aspartic acid, arginine, glycine, valine and the like. When the constituent amino acid before substitution is cysteine, the newly introduced amino acid is preferably, for example, a neutral amino acid. Examples of the neutral amino acid may include, for example, glycine, valine, alanine, leucine, isoleucine, tyrosine, phenylalanine, histidine, tryptophan, serine, threonine methionine and the like. Particularly preferred are serine and threontne. When the constituent amino acid before substitution is other than cysteine, the newly introduced amino acid is, for example, selected from those different in hydrophilic or hydrophobic properties, or electric charge from the original amino acid before substitution. When the constituent amino acid before substitution is aspartic acid, examples of the newly introduced amino acid may include asparagine, threonine, valine, phenylalanine, and arginine, and most preferably asparagine and arginine.

When the constituent amino acid before substitution is arginine, the introduced amino acid may include glutamine, threonine, leucine, phenylalanine, and aspattic acid, and most preferably glutamine. When the constituent amino acid before substituiton is glycine, the introduced amino acid may include threonine, leucine, phenylalanine, serine, glutamic acid, argintne and the like, and most preferably threonine. When the constituent amino acid before substitution is serine, the introduced amino acid may include methionine, alanine, leucine, cysteine, glutamine, arginine, aspattic acid and the like, and most preferably methionine.

When the constituent amino acid before substitution is valine, the introduced amino acid may include serine, leucine, proline, glycine, lysine, aspartic acid and the like, and most preferably, serine.

The constituent amino acid before substitution may include preferably aspattic acid, alginine, glycine, serine and valine. The introduced amino acid may include preferably asparagine, glutamine, arginine, threonine, methionine, serine, and leucine. Most preferred are substituted muteins in which cysteine, a constituent amino acid, is replaced by serine.

In said substitution there may be two or more substitutions simultaneously. Most preferred is the substitution of 2 or 3 constituent amino acids. The mutein can result from one or more of tile combinations of the abovementioned additions, deletions and substitutions.

The present invention may be used for the production of human aFGF mutein comprising one or more substitutions of the cysteine residues at positions 16, 83 and 17 of mature human aFGF with other amino acid(s) and-/or an additional methionine attached to the first amino acid at the N-terminus of mature human aFGF.

Furthermore, the present invention may be used for the production of bovine aFGF mutein comprising one or more substitutions of the cysteine residues at position 16, 47 and 83 of mature bovine aFGF with other amino acid(s) and/or an additional methionine attached to the first amino acid at the N-terminus of mature bovine aFGF.

Further, the present invention may be used for the production of said human and/or bovine aFGF mutein(s) comprising 139, 140 or 154 amino acids.

The mutein comprising 139 amino acids is equivalent to the 140 amino acid form with the amino terminal phenylalanine residue removed.

The mutein comprising 154 amino acids is equivalent to a mutein which contains the following additional amino acids: Ala-Glu-Gly-Glu-Ile-Thr-Thr-Phe-Thr-Ala-Leu-Thr-Glu-Lys with the C-terminus Lys attached to the N-terminus Phe at the first position of the 140 amino acid from (EP No.0319052).

The method according to the present invention is unexpectedly advantageous in producing human aFGF protein.

For the preparation of said muteins, site-directed mutagenesis is applicable and useful. This technique is well known in the literature, for example, Lather, R. F. and Lecoq, J. P., Genetic Engineering, Academic Press (1983), 31–50. The mutagenesis directed on oligonucleotides is described in Smith, M. and Gillam, S, Genetic Engineering; Principle and Method, Plenum Press (1981) Vol. 3, 1–32. The structural genes encoding the muteins may be prepared by, for example, (a) hybridizing a single-stranded DNA comprising a single strand of aFGF structural gene, with a oligonucleotide primer having mutation (the primer is complementary to a region comprising a codon for cysteine to be replaced or, as the case may be, an anti-sense triplet pairing with the codon for cysteine, except that mismatches with codons for other amino acids, and, as the case may be, antisense.triplets are permitted (b) elongating the primer with DNA polymerase to form a heteroduplex having the mutation, and (c) replicating the heteroduplex with the mutation.

A phage DNA carrying the mutated gene is then isolated and inserted into a plasmid. The plasmid thus obtained is used to transform an appropriate host (for example, E. coli) to obtain a transformant. T7 promoters used for the invention may be any of T7 promoters found on T7 DNA [J. L. Oakley et al, Proc. Natl. Acad. Sci. U.S.A. 74, 4266–4270 (1977), M. D. Rosa, Cell, 16, 815–825 (1979), N. Panayotatos et al. Nature 280, 35 (1979), J. J. Dunn et al, J. Mol. Biol. 166, 477–535 (1983)] and preferably $\phi$10 promoter [A. H. Rosenberg etal. Gene, 56, 125–135 (1987)]. Transcription terminators used for the invention may be any of terminators capable of working in an E. coli system, and preferably T $\phi$ terminator [F. W. Studlet et al., J. Mol. Biol. 189, 113–130 (1986)]. T7 RNA polymerase genes may include T7 gene 1 [F. W. Studier et al., J. Mol. Biol. 189, 113–130 (1986)]. Vectors from which vectors used in the invention are derived may include, for example, pBR322, pUC8, pUC9, pMB9, pKC7, pACYC177, pKN410 and the like. The vectors used in the invention are constructed by recombination of T7 promoters and T7 terminators into the above described vectors. Such vectors may be pET-1, pET-2, pET-3, pET-4 and pET-5 [A. H. Rosenberg, Gene 56, 125–135 (1987)], and preferably pET-3c and pET-8c [supra]. Hosts used for transformants in the invention may include any of E. coli strains incorporated with T7 RNA polymerase gene (T7 gene 1) [F. W. Studier et al., J. Mol. Biol. 189, 113–130 (1989)], for example, MM294, DH-1, C600, BL21, etc.

Preferably used are MM294 strain and BL21 strain wherein T7 gene 1 inserted $\lambda$ phages are lysogenized.

Promoters for T7 gene 1 may be promoters capable of inducing an expression, for example, lac, recA, trp and the like, and preferably a lac promoter. Transformants used in the invention can be obtained by transforming the T7 gene 1 (RNA polymerase gene) incorporated E. coli with plasmids carrying T7 promoters, genes to be expressed and transcription terminators according to conventional methods such as the methods disclosed in Proc. Natl. Acad. Sci., USA, 69, 2110 (1972), Gene, 17, 107 (1982), etc.

In certain preferred embodiments, the hosts used are previously transformed with plasmids carting T7 lysozyme genes and thereby the resulting transformant may carry two different plasmids simultaneously.

Methods of cultivation of the transformants are conventional. The liquid medium is suitable for the medium used for cultivation. The liquid medium may contain a carbon source, a nitrogen source, minerals and the like. The carbon source may include, for example, glucose, dextrin, soluble starch, sucrose, etc. The nitrogen source may include inorganic or organic materials such as ammonium salts, nitrate salts, cornsteep liquor, pepton, casein, meat extracts, soy bean cakes, potato extracts, etc. The mineral may include, for example, calcium chloride, sodium dihydrogenphosphate, magnesium chloride, etc.

Further yeast extracts, vitamins, growth promoting factors, etc may be supplemented. The pH of medium can vary preferably from about 6 to about 8. The medium used for culturing the transformant E. coli may include preferably, for example, M9 medium containing glucose and casamino acid [Miller, Journal of Experiments in Molecular Genetics, 431–433, Cold Spring Harbor Laboratory, New York (1972)].

According to necessity, for working the promoter efficiently, reagents such as, for example, 3$\beta$-indolyl acrylic acid and isopropyl thiogalactopyranoside may be added.

Cultivation can be carried out usually at temperatures of from about 15° to 43° C. for about 3 to about 24 hours, and as the case may be, aeration and/or agitation may also be added.

Purification of the aFGF protein from the culture can be conducted, for example, according to the following method.

Methods for extracting the aFGF protein from the cultured micro-organisms or cells, may include a method comprising collecting the microorganisms or cells in a conventional manner after cultivation, and then eluting the subject protein out of the cell by suspending the microorganisms or cells in a buffer containing protein denaturing agents such as guanidine hydrochloride, a method comprising disrupting the microorganism or the cell by french press, sonication, lysozyme, and/or freezing-thawing and then obtaining the aFGF protein by centrifugation, etc.

Particulary preferable are the french press method and the combined method of lysozyme and sonication. A method for purifying the aFGF protein from the supernatant can be conducted by combining suitably known isolations and purifications per se.

The isolations and purifications may include a method utilizing solubilities such as salting-out, solvent precipitation and the like, a method utilizing mainly differences of molecular weight such as dialysis, ultrafiltration, gel filtration and SDS-poly acrylamide gel electrophoresis and the like, a method utilizing differences of charge such as ion-exchange chromatography and the like, a method utilizing specific affinities such as affinity chromatography and the like, a method utilizing differences of hydrophobicity such as reversed phase high-performance liquid chromatography and the like, a method by the use of differences of tsoelectric point such as tsoelectric electrophoresis and the like. The application of the aFGF protein in the E. coli extracts to affinity chromatography by the use of heparin Sepharose as a carrier is advantageous among the methods for purification of aFGF protein. Purification of aFGF protein can be conducted, for example, by loading the etuate on a heparin Sepharose column equilibrated with a buffer such as Tris and phosphate, at neutral or near pH, followed by elution with a linear gradient such as NaCl and the like after sufficient washing. Particularly useful is a heparin column which has been developed for high performance liquid chromatography (for example, Shodex AF-pak HR. 894, Showadenko K. K.). In a similar fashion of the heparin Sepharose column, the aFGF protein can be recovered as an approximately homogeneous product by loading the sample thereon in a neutral or near buffer followed by elution with a linear Gradient such as NaCl and the like after sufficient washing. The product thus obtained can be subjected to dialysis and lyophilization to give a dry powder. Preferred is the preservation of the lyophilized product by adding serum albumin and the like as a stabilizer because adsorption of the product to a container can be prevented.

During purification or preservation processes, the presence of a slight amount of a reducing agent in admixture therewith is useful for prevention of oxidation thereof. The reducing agents may include β-mercaptoethanol, dithiothreitol, glutathione and the like.

Substantially pyrogen and endotoxin-free, substantially pure aFGF proteins can be obtained.

The substantially pure aFGF protein according to the present invention includes products in which aFGF protein content is more than 95% (w/w), and more preferably, products in which aFGF protein content is more than 98% (w/w).

The aFGF protein thus obtained can be used, for example as a cure promoting agent for burns, wounds, etc. Furthermore since it posseses growth promoting activity of nerve cells, it is useful in treating various neuropathies.

For its pharmaceutical use, the aFGF can be safely administered to warm-blooded mammals (e.g. humans, mice, rats, hamsters, rabbits, dogs, cats) parenterally or orally either in a powder form per se or in the form of pharmaceutical compositions (e.g. injections, tablets, capsules, solutions, ointments) in admixture with pharmaceutical acceptable carriers, excipients and/or diluents. The pharmaceutical compositions can be formulated in accordance with a conventional method.

When used for the above pharmaceutical purposes, the aFGF is administered, for example, to the above warm-blooded mammals in an appropriate amount selected from the range of from about 10 ng to 10 μg/kg body weight a day according to route of administration, reaction sensitivities, severity of the disease, etc.

Further, the aFGF protein thus purified can be used as a reagent for promoting cell cultivation. In this instance, the aFGF protein is added to the medium preferably in an amount of about 0.1 to 10 μg per liter of medium.

The following transformants which were obtained in the Examples mentioned below were deposited at the Institute for Fermentation, Osaka, Japan (IFO), and at the Fermentation Research Institute, Agency of Industrial Science and Technology, Ministry of International Trade and Industry, Japan (FRI) under the Bundapest Treaty.

Their accession numbers on the deposit dates are shown in Table 1 below (The deposit dates are indicated in parenthesis).

TABLE 1

| Transformant | IFO | FRI |
| --- | --- | --- |
| E. coli MM294(DE3)/ pLysS, pTB 975 (Example 1) | IFO 14936 (September 12, 1989) | FERM BP-2599 (September 20, 1989) |
| E. coli MM294(DE3)/ pLysS, pTB 1069 (Example 2) | IFO 14937 (September 12, 1989) | FERM BP-2600 (September 20, 1989) |
| E. coli MM294(DE3)/ pLysS, pTB 1070 (Example 2) | IFO 14938 (September 12, 1989) | FERM BP-2601 (September 20, 1989) |

In the specification and drawings of the present application, the abbreviations used for bases, amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.
DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine trlphosphate
dGTP: Deoxyguanosine triphosphate
dCTP: Deoxycytidine triphosphate
ATP: Adenosine triphosphate
Tdr: Thymidine
EDTA :Ethylenediamlne tetraacetic acid
SDS: Sodium dodecyl sulfate
Gly: Glycine
Ala: Alanine
Val: Valine
Leu: Leucine
Ile: Isoleucine
Set: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine The numbering of constituent amino acids in human and bovine aFGFs used therein is in accordance with that described in Biochemical and Biophysical Research Communications Vol. 138, 611–617 (1986).

EXAMPLE

The invention is further illustrated by the following examples. These examples are not intended to limit the invention in any manner.

Example 1

Preparation of aFGF (a) Construction of Plasmid for Expression

Figure 1:
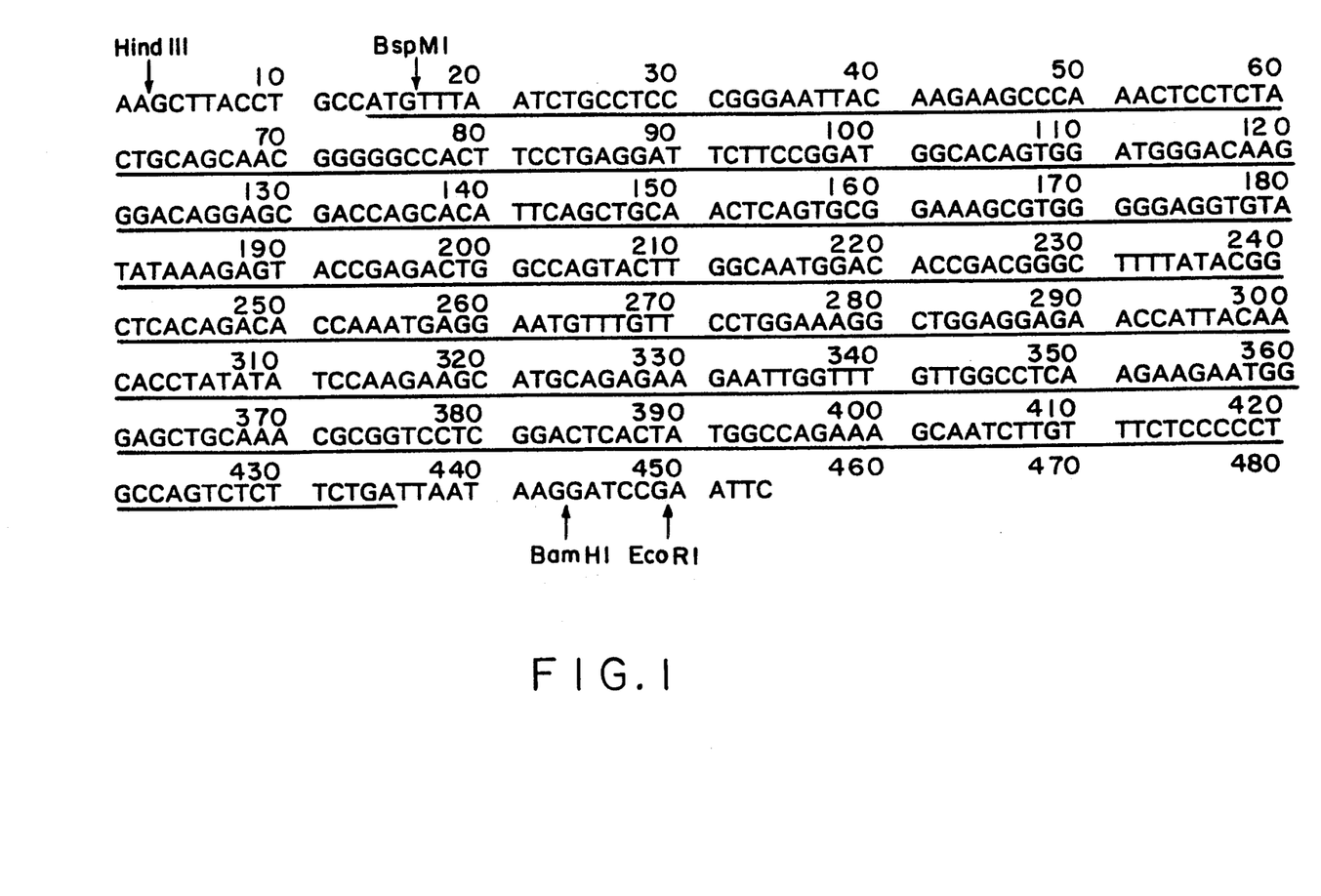
FIG. 1 depicts a cDNA sequence of human aFGF used in Example 1.

Plasmid pTB917 carrying chemically synthesized cDNA of human aFGF (FIG. 1) in pUC18 (Methods in Enzymology, 101, 20–78 (1983)) was digested with BspMI and treated with DNA polymerase large fragment to create blunt ends followed by digestion with BamHI to produce a 0.45 kb DNA fragment.

Figure 2:
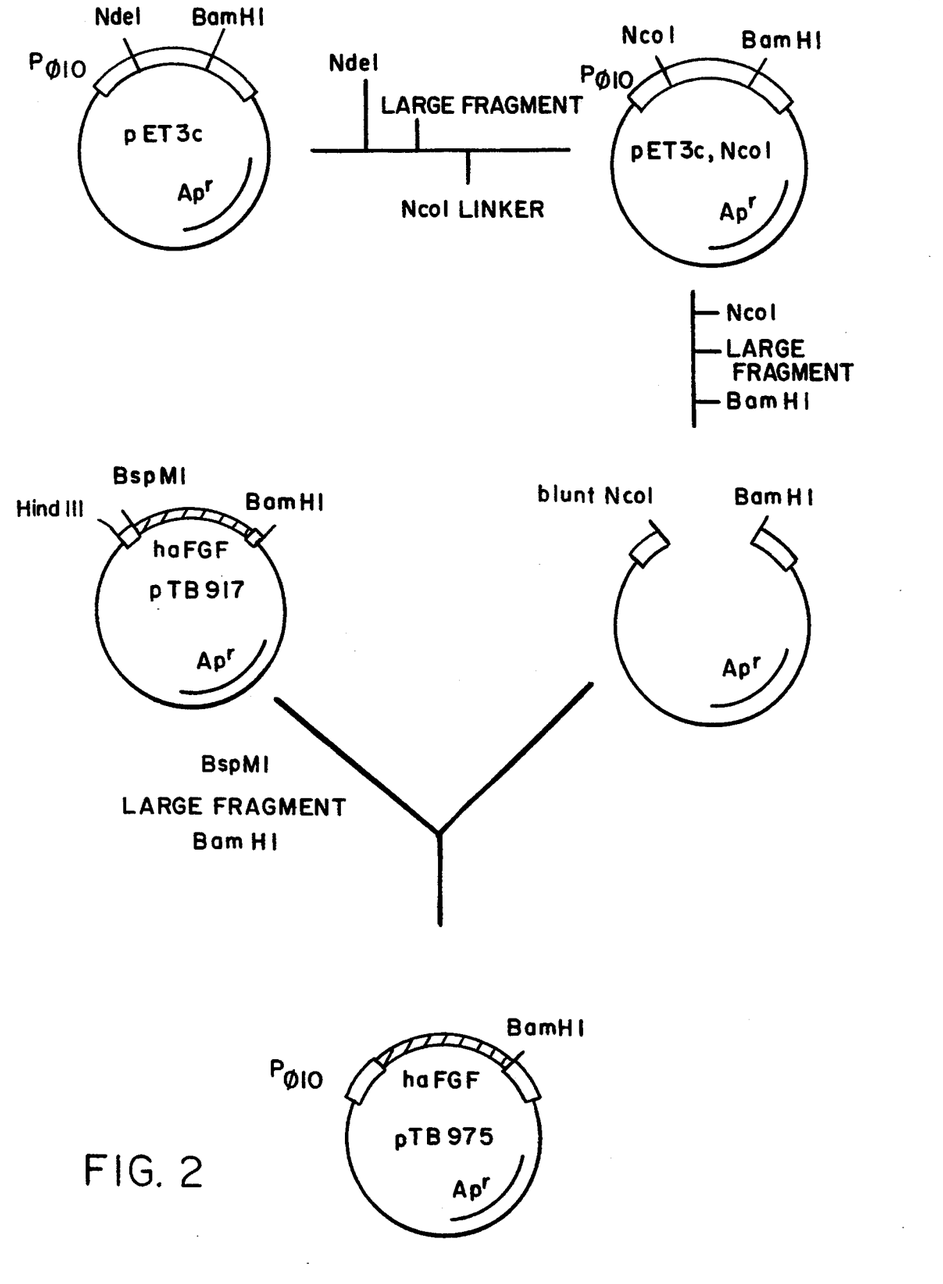
FIG. 2 shows a schematic illustration for construction of plasmid pTB975 obtained in Example 1.

Plasmid pET-3c carrying φ 10 promoter of T7 phage (Studeer, F. W. et al., J. Mol. Biol. 189, 113–130 (1986), Gene 56, 125–135 (1987)) was used for a vector DNA. The pET-3c was cleaved with NdeI and treated with DNA polymerase large fragment to create blunt ends followed by ligation of NcoI linkers, 5'-CCATGG-3' with T4 DNA ligase. The resulting plasmid was cleaved with NcoI and blunt-ended with DNA polymerase large fragment followed by cleavage with BamHI to remove S10 sequences. The resulting fragment was ligated with T4 DNA ligase to the 0.45 kb blunt-ended BspMI-BamHI fragment to give pTB975 (FIG. 2).

(b) Expression of Human aFGF cDNA in E. coli

λ phage DE 3 having T7 phage RNA polymerase gene [Studier, F. W. et al., J. Mol. Biol., 189, 113–130 (1986)] was lysogenized in E. coli MM 294 strains followed by transfection of plasmid pLysS carrying T7 phage lysozyme gene [Studier, F. W. et al., J. Mol. Biol. 189, 113–130 (1986)] to produce E. coli MM294 (DE3)/pLysS strains. The E. coli strain was transformed with pTB975 to give E. coli MM294 (DE3)/pLysS, pTB975 (IFO 14936, FERM BP-2599).

The transformant was incubated in a medium containing 35 μg/ml of ampicillin and 10 μ/g/ml of chloramphenicol at 37° C. When the turbidity reached to Klett 170, isopropyl β-D-thiogalactoside (IPTG) was added to finally 0.5 mM. Incubation was continued for additional three hours.

The transformants were harvested by centrifugation, washed with PBS cooled in ice, recollected, and stored at −20° C. until use.

(c) Purification of Human aFGF

The microorganisms collected from 1 liter of culture were suspended in 100 ml of ice-cooled 10 mM Tris-HCl (pH 7.4) containing 10 mM EDTA, 0.6M NaCl, 10% sucrose and 0.25 mM PMSF, and egg white lysozyme was added to 0.5 mg/ml. The suspension was allowed to stand in ice for an hour, incubated at 37° C. for five minutes, sonicated (20 sec, twice), whilst ice cooling, and centrifuged (SORVALL, 18K rpm, 30 min., 4° C.) to give a supernatant. The supernatant was mixed with 200 ml of ice-cooled 20 mM Tris-HCl (pH 7.4) containing 1 mM EDTA, and applied to a heparin Sepharose column (2.5×4 cm) equilibrated in 20 mM Tris-HCl (pH 7.4) containing 1 mM EDTA and 0.2M NaCl. The column was washed with 150 ml of 20 mM Tris-HCl (pH 7.4) containing 1 mM EDTA and 0.5M NaCl, and then protein eluted with 20 mM Tris-HCl (pH 7.4) containing 1 mM EDTA and 1.5M NaCl.

Figure 3:
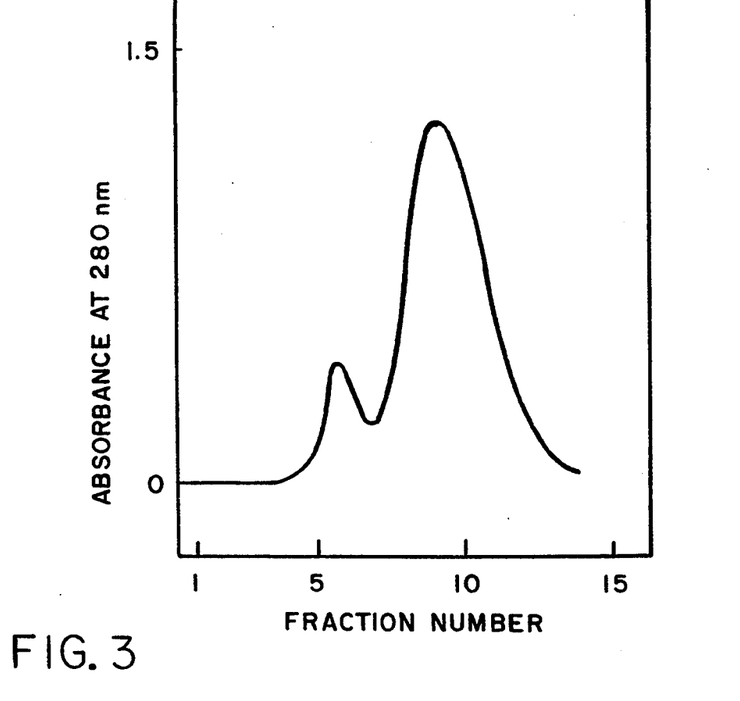
FIG. 3 depicts an elution profile obtained in Example 1.

Six ml fractions were collected, monitored at OD$_{280}$ and the second peak fractions (No. 8–11, total 24 ml) pooled (FIG. 3).

Twenty two ml of the eluate was mixed with an equivalent amount of 20 mM Tris-HCl (pH 7.4) containing 1 mM EDTA and 2M (NH$_4$)$_2$SO$_4$, and applied to a phenyl-Sepharose column (2.5×8 cm) equilibrated with 20 mM Tris-HCl (pH 7.4), containing 1 mM EDTA and 1M (NH$_4$)$_2$SO$_4$ (flow rate: 0.5 ml/min.).

The column was washed with 20 ml of the same buffer, and eluted with a linear gradient of from 1M to 0M ammonium sulfate (folow rate: 0.5 ml/min, for 200 min).

Figure 4:
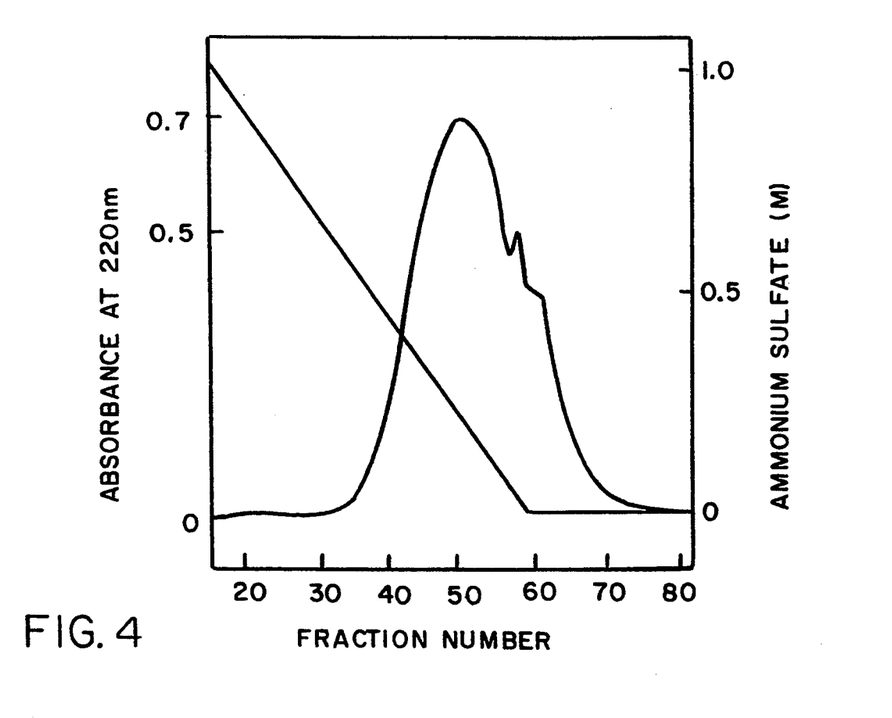
FIG. 4 depicts an elution profile obtained in Example 1.

Fractions 40–45 were collected (FIG. 4) as a purified aFGF.

(d) Reversed-Phase C4 HPLC

The solution (1.2 mg/ml) of purified human aFGF was mixed with 0.25 m. of 0.1% trifluoroacetic acid (TFA), applied on a reversed-phase C4 clumn (VYDAC), and eluted with a linear gradient of 0%–90% acetonitrile in 0.1% TFA.

Figure 5:
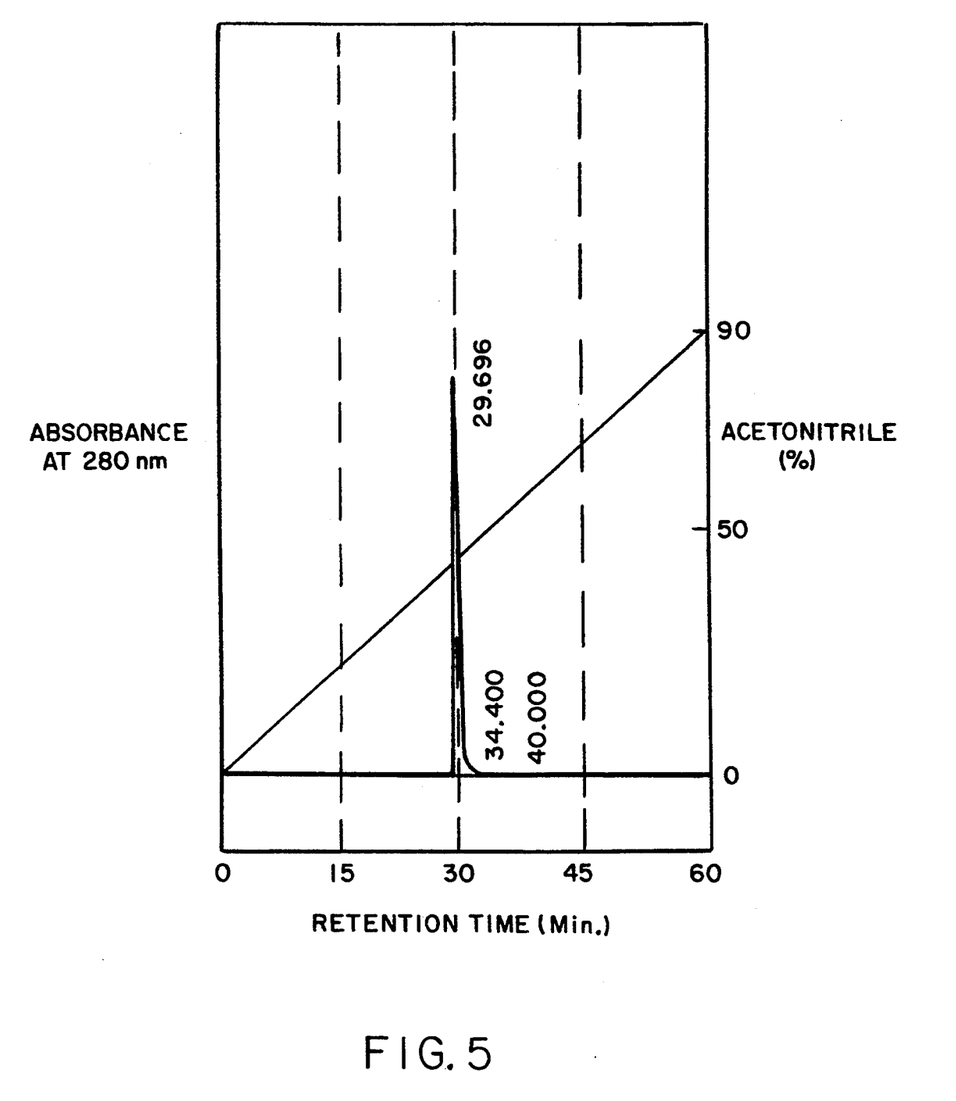
FIG. 5 depicts an elution profile obtained in Example 1.

The elution pattern was examined. The elution was performed at 1 ml/min of flow rate for 60 min (FIG. 5).

(e) Biological Activity

Activity of human aFGF was assayed by the determination of $^3$H-thymidine incorporation into DNA of murine BALB/c 3T3 cell lines, in accordance with the method of Sasada, et al. (Mol. Cell Biol. 8, 588–594 (1988)). Upon addition of the sample, depending on necessity, a heparin solution (SIGMA Grade I) was added to media and the sample.

Example 2

Figure 6:
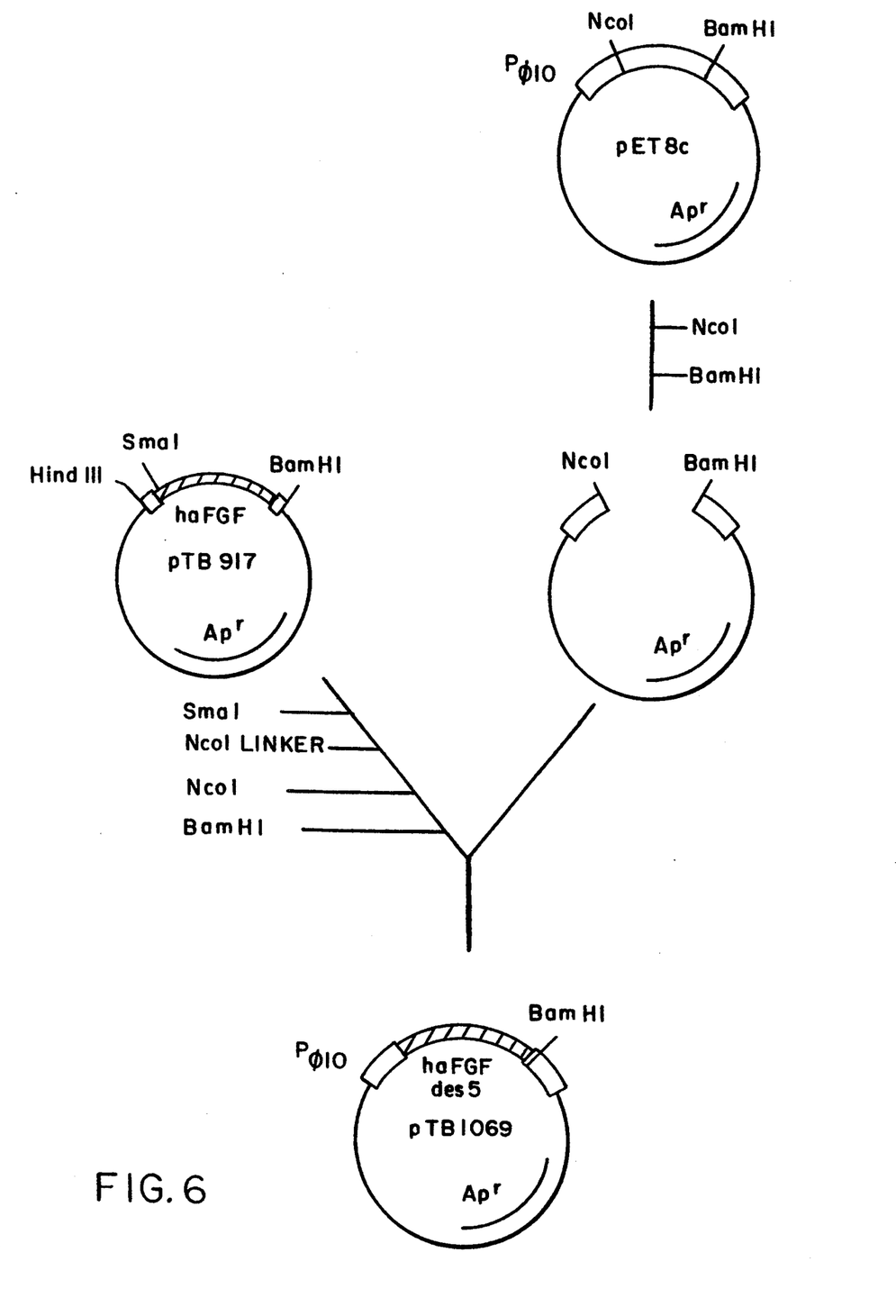
FIG. 6 shows a schematic illustration for construction of plasmid pTB1069 for the expression of 5 amino terminal residue-deleted aFGF obtained in Example 2.
Figure 7:
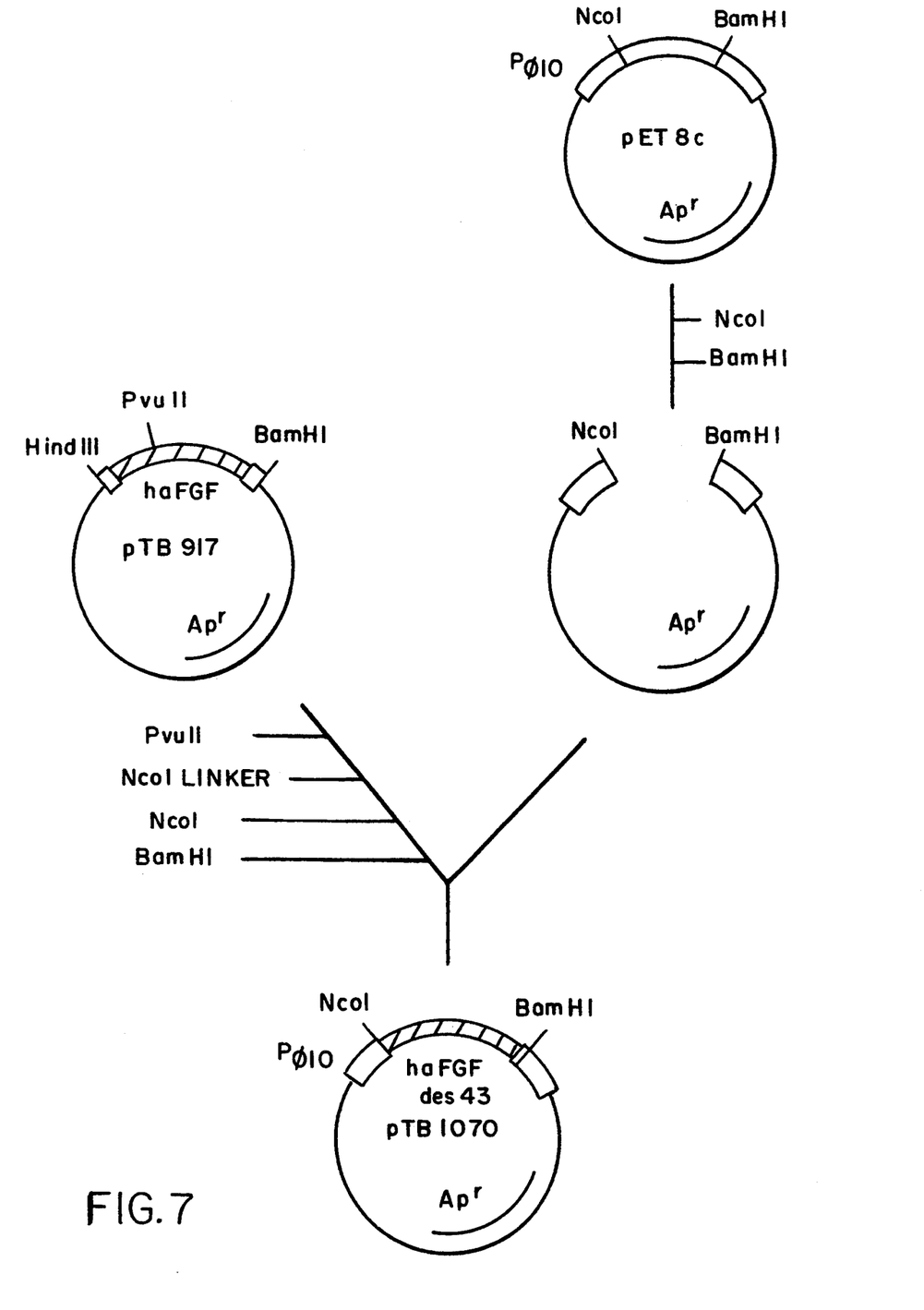
FIG. 7 shows a schematic illustration for construction of plasmid pTB1070 for the expression of 43 amino terminal residue-deleted aFGF obtained in Example 2.

Preparation of Recombinant Human aFGF Mutein Deleted Amino Termini (a) Construction of Plasmid for Expression Plasmid pTB917 carrying chemically synthesized cDNA of human aFGF (FIG. 1) in pUC18 [Method in Enzymology, 101, 20–78 (1983)] was cleaved with either SmaI (FIG. 6) or PuvII (FIG. 7), followed by ligation of NcoI linkers, 5'-CCATGG-3' with T4 DNA ligase. These plasmids were cleaved with NcoI and BamHI to prepare 0.41 kb and 0.3 kb DNA fragments. pET8c carrying T7 phage φ 10 promoter (given by Studier, F. W. (Brook haven National Labs U.S.A.), this pET-8c is described in J. Mol. Biol., 189, 113–130 (1985) and Gene, 56, 125–135 (1987)) was used for a vector DNA. The pETSC was cleaved with NcoI and BamHI, followed by ligation of the 0.41 kb DNA fragment and the 0.3 kb thereto with T4 DNA ligase to obtain pTB1069 (FIG. 6) and pTB1070 (FIG. 7), respectively.

(b) Expression of haFGF cDNA Deleted Amino Termini in E. coli

λ phage DE3 having T7 phage RNA polymerase gene [Studier, F. W. et al., J. Mol. Biol., 189, 113–130 (1986)] was lysogenized in E. coli MM 294 strains follwed by transfection of pLysS carrying T7 phage lysozyme gene [Studier, F. W. et al., J. Mol. Biol. 189, 113–130 (1986)] to produce E. coli MM294 (DE3)/pLysS strains.

The E. coli strain was transformed with pTB1069 and pTB1070 to give E. coli MM294 (DE3)/pLys S, pTB1069 (IFO 14937, FERM BP-2600) and E. coli MM294 (DE3)/pLys S, pTB1070 (IFO 14938, FERM BP-2601), respectively.

The transformant was Incubated in a medium containing 35 μg/ml of ampicillin and 10 μg/ml of chloramphenicol at 37° C. When the turbidity reached to Klett 120, isopropyl β-D-thiogalactoside was added to finally 0.5 mM. Incubation was continued for additional two hours. The transformants were harvested by centrifugation, washed with phosphate buffered saline (PBS) cooled in ice, then recollected, and stored at −20° C. until use.

(c) Purification of Five Amino Terminal Residue-deleted haFGF

E. coli MM294 (DE3)/pLys S, pTB 1069 (IFO 14937, FERM BP-2600) collected from 75 ml of the culture was suspended in 10 ml of ice-cooled 10 mM Tris-HCl (pH 7.4) containing 10 mM EDTA, 0.2M NaCl, 10% sucrose and 0.25 mM phenylmethylsulfonyl fluoride (PMSF) followed by addition of egg white lysozyme to 0.5 mg/ml.

Figure 8:
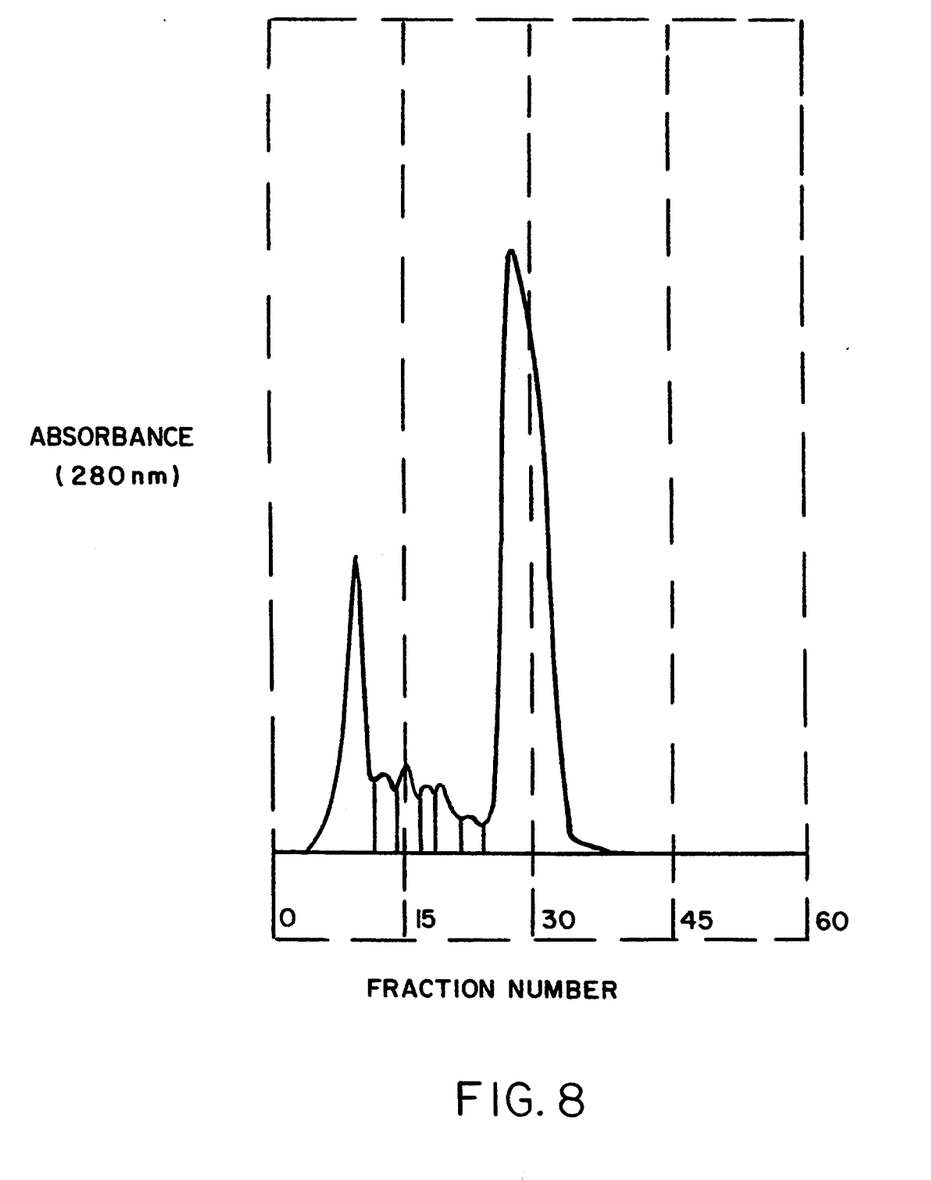
FIG. 8 depicts an elution profile from a heparin HPLC column used for purification of 5 amino terminal residue deleted aFGF obtained in Example 2.

The suspension was allowed to stand in ice for an hour, then incubated at 37° C. for 5 min., sonicated whilst ice cooling and centrifugated (SORVALL, 18K rpm, 30 min, 4° C.) to give a supernatant. The supernatant was applied to a heparin HPLC column (0.8 cm×5 cm) equilibrated with 20 mM Tris-HCl (pH 7.4). The column was washed with 20 mM Tris-HCl (pH 7.4) containig 0.6M NaCl, eluted with a linear gradient of 0 to 2M NaCl (flow rate: 1 ml/min. for 1 hr.) and 1 ml fractions were collected. The eluted fractions 28–32 were pooled (FIG. 8). Five amino acid residue deleted human aFGF (4.2 mg) was obtained by the above procedures.

(d) Purification of 43 Amino Terminal Residue Deleted haFGF

E. coli MM294 (DE3)/pLysS, pTB 1070 (IFO 14938, FERM BP-2601) collected from 125 ml of the culture was suspended in 10 ml of ice-cooled 10 mM Tris-HCl (pH 7.4) containing 10 mM EDTA, 0.2M NaCl, 10% sucrose, and 0.25 mM PMSF followed by addition of egg white lysozyme to 0.5 mg/ml.

The suspension was allowed to stand in ice for an hour, then warmed to 37° C. for 5 min., sonicated whilst ice cooling and centrifugated.

The precipitate was suspended in 2M NaCl followed by recentrifugation to give a precipitate which was suspended in 15 ml of 20 mM Tris-HCl (pH 7.4) containing 6 M urea and 10 mM DTT and incubated in ice for 3 hr whilst intermittently stirring. The resulting solution was centrifugated to give a supernatant which was applied to a Q-Sepharose column (2.5 cm ×8 cm) equilibrated with 20 mM Tris-HCl (pH 7.4) containing 3M urea.

Figure 9:
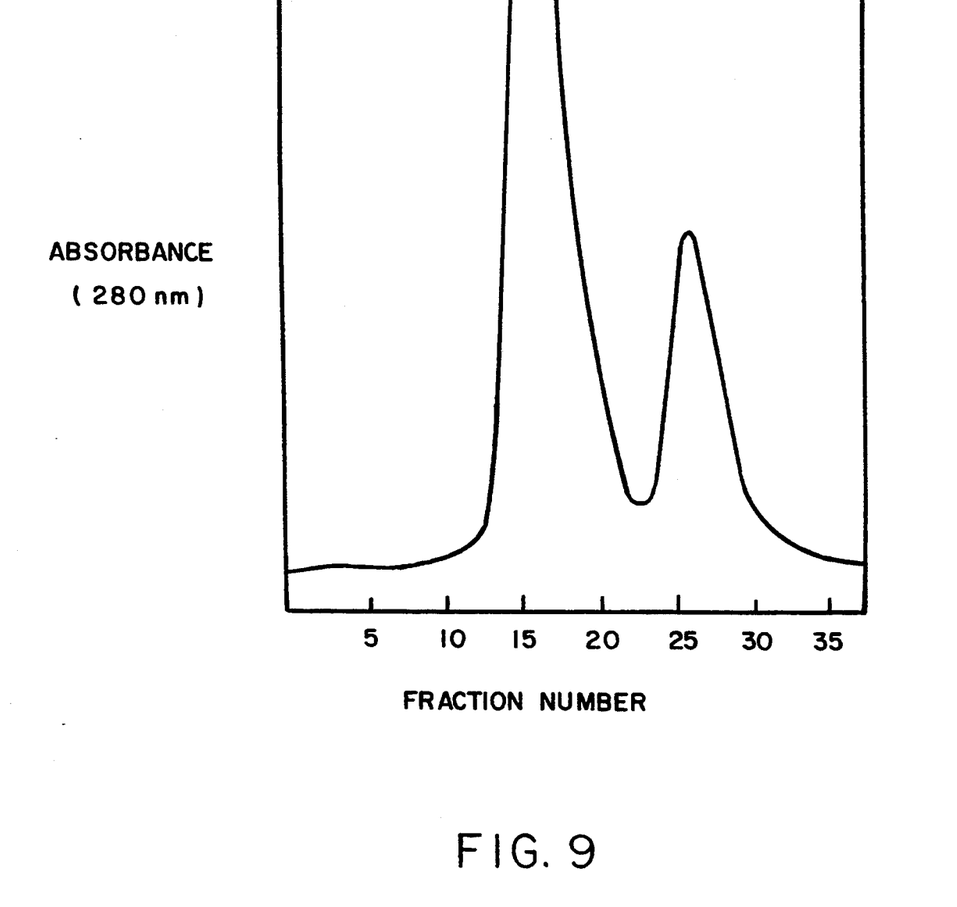
FIG. 9 depicts an elution profile from a Q Sepharose column used for purification of 43 amino terminal residue deleted aFGF obtained in Example 2.

The column was washed with a buffer used for equilibrating, eluted with a linear gradient of 0M–1M NaCl at a flow rate of 0.6 ml/min. for 160 min. and 2.5 ml fractions were collected (FIG. 9). The eluted fractions 14–19 were pooled and dialyzed against 2 l of 20 mM Tris-HCl (pH 7.4) containing 5 mM DTT overnight followed by 3 l of 20 mM Tris-HCl (pH 7.4) containing 1 mM DTT for 3 hr. Fourty three amino acid terminal residue deleted human aFGF (3.2 mg) was obtained by the above procedures.

Example 3

Figure 10:
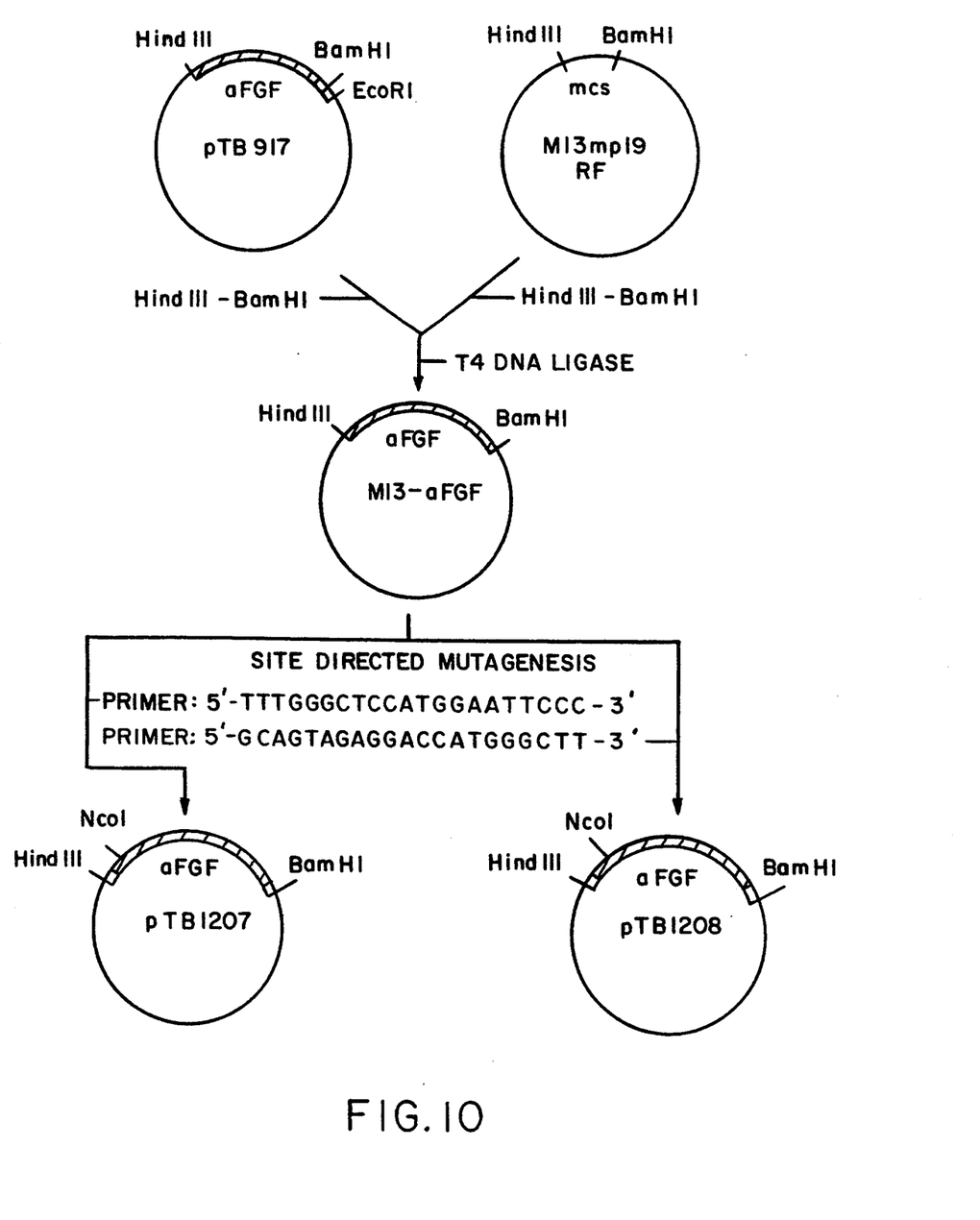
FIG. 10 shows a schematic illustration for construction of plasmids pTB1207 and pTB1208 which are obtained in Example 3.

Preparation of Recombinant haFGF Mutein Deleted 9 Amino Acid Terminal Residues and Recombinant haFGF Mutein Deleted 12 Acid Amino Terminal Residues (a) Construction of Plasmid For Expression Plasmid pTB917 inserted with human aFGF cDNA (FIG. 1) is digested with Hind III and Bam HI to cut out a cDNA portion which is inserted into a Hind III-Bam HI site of RF DNA in M13 mp 19 phagges (Gene 33; 103–119 (1985)) with T4DNA ligase (FIG. 10). From the resulting phage the single stranded DNA is prepared into which mutagenesis is introduced by the use of primers 5'-TTTGGGCTCCATGGAATTCCC-3' and 5'-GCAGTAGAGGACCATGGGCTT-3' to obtain pTB1207 and pTB1208, respectively (FIG. 10.) For the reaction of site directed mutagenesis, mutagenesis kits purchased from AMASHAM (U.K.) are used.

Figure 11:
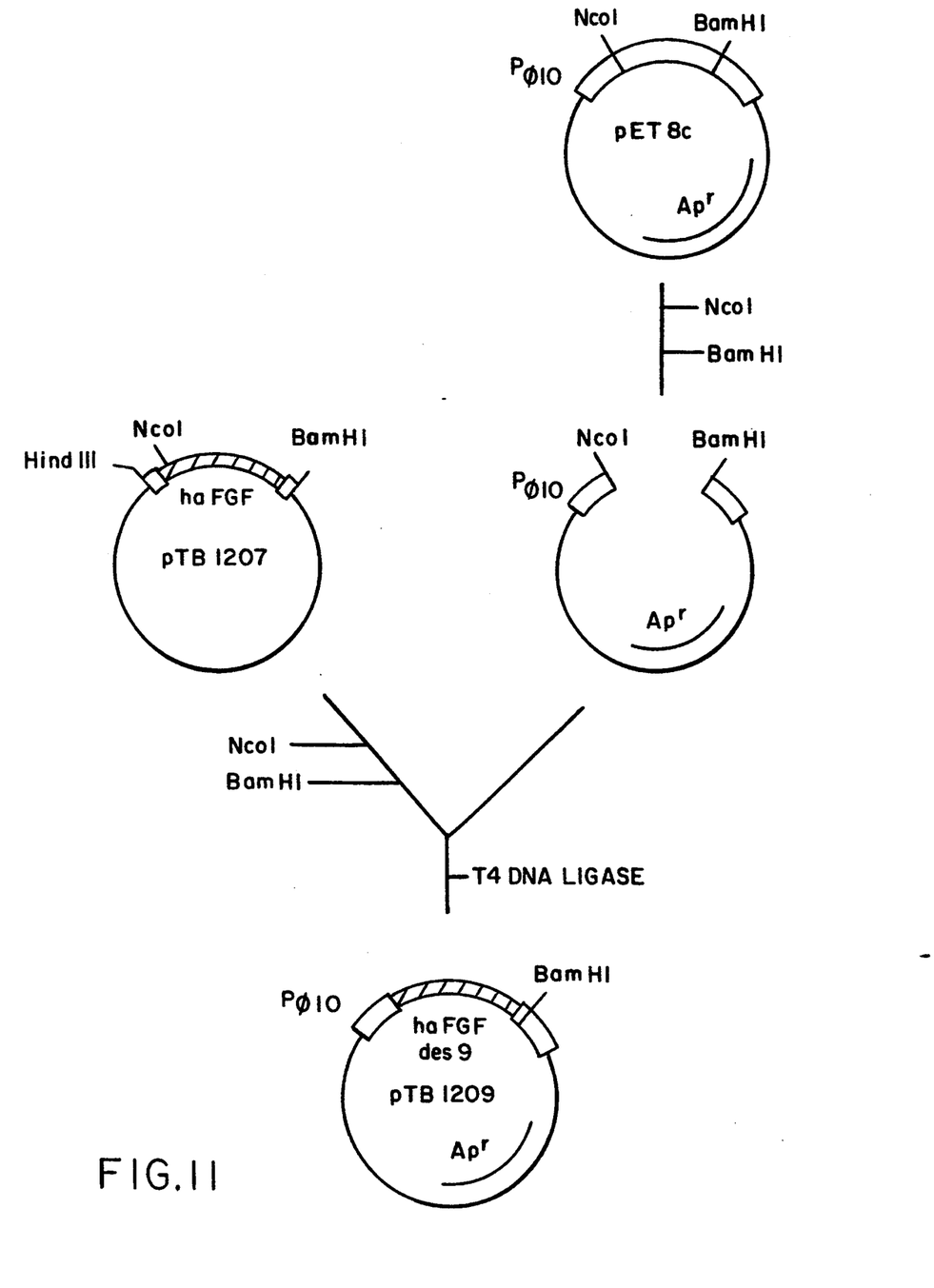
FIG. 11 shows a schematic illustration for construction of plasmid pTB1209 for the expression of 9 amino terminal residue-deleted aFGF which is obtained in Example 3.
Figure 12:
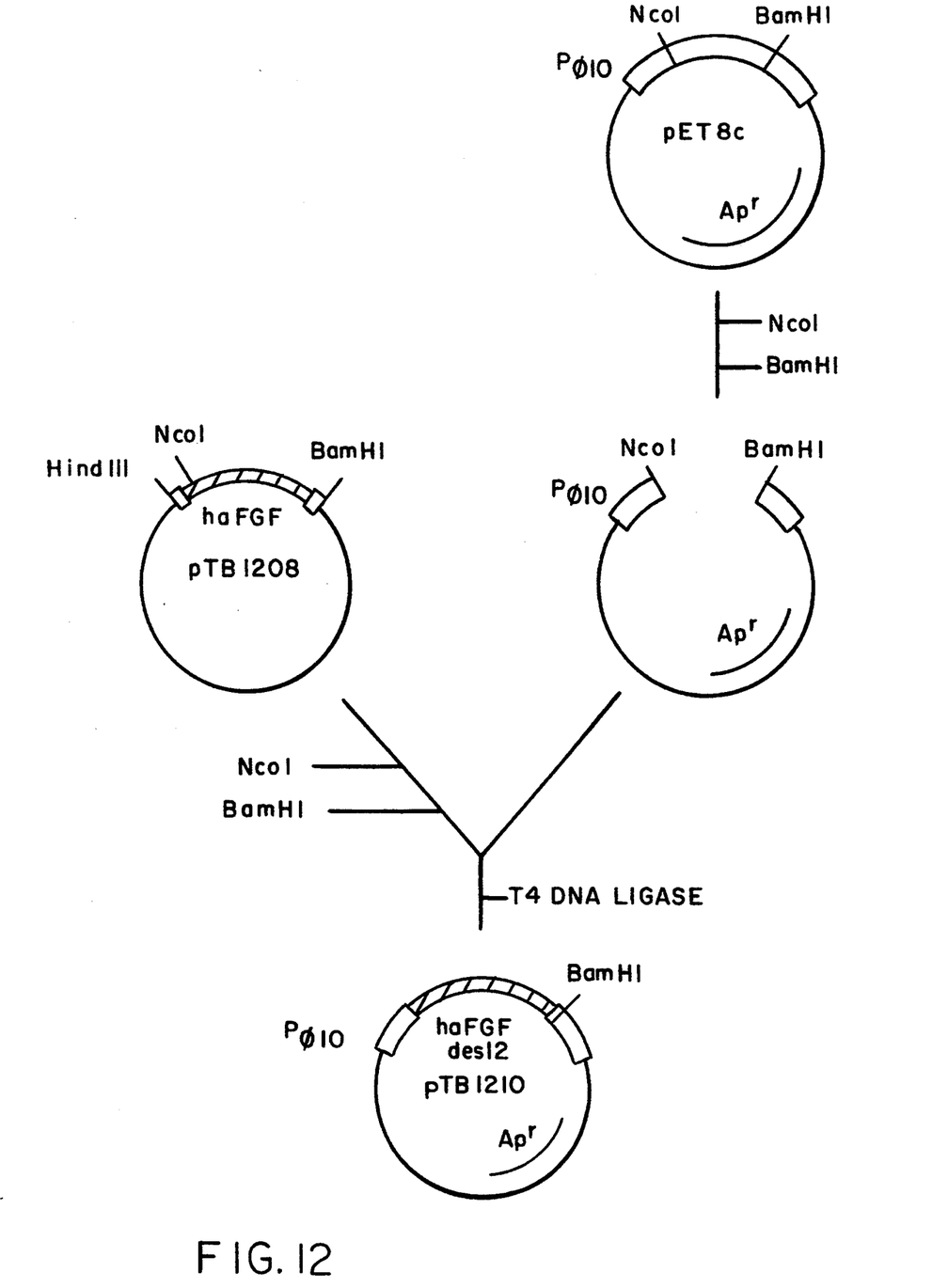
FIG. 12 shows a schematic illustration for construction of plasmid pTB1210 for the expression of 12 amino terminal residue-deleted aFGF which is obtained in Example 3.

The plasmids pTB1207 DNA and pTB1208 DNA are digested with NcoI and BamHI to cut out mutated aFGF cDNAs which are inserted into a NcoI-BmaHI site of said plasmid pET-8c carrying T7 phage φ 10 promoter (J. Mol. Biol. 189, 113–130 (1986) and Gene 56, 125–135 (1987)) to obtain plasmids pTB1209 for expression of 9 amino terminal deleted-type mutein and pTB1210 for expression of 12 amino terminal deleted-type mutein, respectively (FIG. 11 and FIG. 12).

(b) Expression of haFGF cDNA Deleted Amino Termini in E. coli

λ phage DE3 having T7 phage RNA polymerase gene [Studier, F. W. et al. J. Mol. Boil: 189, 113–130 (1986)] is lysogenized in E. coli MM294 strains followed by transfection of plasmid pLysS carrying a T7 phage lysozyme gene [Studier F. W. et al, J. Mol. Boil. 189, 113–130 (1986) to give Escherichia coli MM294 (DE3)/pLysS. The E. coli is transformed with pTB1209 and pTB1210 to produce E. coli MM294 (DE3)/pLysS, pTB1209 and MM294 (DE3)/pLysS, pTB1210, respectively. The transformants are cultured in a medium containing 35µg/ml of ampicillin and 10 µg/ml chloramphenicol at 37° C., and when the turbidity reaches to Klett 120, isopropyl β-D-thiogalactoside is added to 0.5 mM in a final concentration followed by cultivation for additional 2 hours. The microorganisms are harvested by centrifugation, washed with phosphate buffered saline (PBS) cooled in ice, then recollected, and stored at −70° C. until use.

A part of the resultant microorganism is used, sonicated, centrifuged to prepare a crude extract which is assyed for biological activities according to the method described in Example 1 (e) to exhibit a significant result.

The following references, which are referred to for their disclosures at various points in this application, are incorporated herein by reference.

1. Biotechnology, 5, 960 (1987)
2. Philip J. Barr, et al. Journal of Biological Chemistry, 263,16471 (1988)
3. D. L. Linemeyer, et al. ICSU Short Reports. Volume 8, Advances in Gene Technology: Protein Engineering and Production, Proceedings of the 1988 Miami Bio/Technology Winter Symposium, IRL Press, page 110
4. Thomas Jnr, kenneth A. et al. EP No. 0 319 052
5. F. Esch, et al. Biochem. Biophys. Res. Commun. 133,554–562, 1985
6. F. W. Studier et al. J. Mol. Biol. 189, 113–130 (1986)
7. Guillermo Gimenez-Gallego, et al. Biochemical and Biophysical Research Communicaitons, Vol. 138, No.2, pp.611–617 (1986)
8. Lather, R. F. and lecoq, J. P., Genetic Engineering, Academic Press (1983), 31–50
9. Smith, M. and Gillam, S. Genetic Engineering; Principle and Method, Plenum Press (1981), Vol. 3, 1–32
10. J. L. Oakely, et al, Proc. Natl. Acad. Sci. U.S.A. 74, 4266–4270 (1977)
11. M. D. Rosa, Cell, 16, 815–825 (1979)
12. N. Panayotatos, et al. Nature 280, 35 (1979)
13. J. J. Dunn et al, J. Mol. Biol. 166, 477–535 (1983)
14. A. H. Rosenberg et al. Gene, 56, 125–135 (1987)
15. Proc. Natl. Acad. Sci., U.S.A., 69,2110 (1972)
16. Gene, 17, 107 (1982)
17. Miller, Journal of Experiments in Molecular Genetics, 431–433, Cold Spring Harbor Laboratory, N.Y. (1972)
18. Methods in Enzymology, 101, 20–78 (1983)
19. Sasada, et al. Mol. Cell Biol., 8, 588–594 (1988)
20. Gene, 33, 103–119 (1985)

What is claimed is:

1. A vector comprising (1) a cDNA sequence encoding a human acidic fibroblast growth factor (haFGF) or a deletion-type mutein of haFGF which lacks UP to 43 amino acids from the N-terminus of haFGF and (2) a T7 promoter which is operably linked into an upstream site therefrom.

2. The vector according to claim 1, which is pTB975.

3. A vector comprising (1) a cDNA sequence encoding a human acidic fibroblast growth factor (haFGF) or a deletion-type mutein of haFGF which is Selected from the group consisting of 1, 5, 8, 9, 11, 12, 20 and 43 amino terminal residue-deleted haFGF and (2) a T7 promoter which is operably linked into an upstream site therefrom.

4. A transformant host cell containing a vector comprising (1) a cDNA sequence encoding a human acidic fibroblast growth factor (haFGF) or a deletion-type mutein of haFGF which lacks up to 43 amino acids from the N-terminus of haFGF and (2) a T7 promoter which is operably linked into an upstream site therefrom.

5. The transformant according to claim 4 which is *E. coli* MM294(DE3)/pLysS, pTB975 (FERM BP-2599).

6. A method for the preparation of a human acidic fibroblast growth factor (haFGF) or a deletion-type mutein of haFGF which lacks up to 43 amino acids from the N-terminus of haFGF which comprises culturing a transformant host cell containing a vector comprising (1) a cDNA sequence encoding an haFGF or said deletion-type mutein and (2) a T7 promoter which is operably linked into an upstream site therefrom in a culture medium to produce and accumulate an haFGF or said deletion-type mutein in the transformed cells, lysing the cells and purifying the protein from resulting haFGF-containing solution or said deletion-type mutein-containing solution.

* * * * *